(12) United States Patent
Fazel et al.

(10) Patent No.: US 11,298,073 B1
(45) Date of Patent: Apr. 12, 2022

(54) DEVICE AND METHOD FOR DETECTION AND TREATMENT OF BRUXISM

(71) Applicant: Delta Neuro Inc., Markham (CA)

(72) Inventors: Payam Fazel, Isfahan (IR); Ahmad Iranban, Shiraz (IR); Niloufar Gheidi, Tehran (IR); Elmira Kiani, Tehran (IR)

( * ) Notice: Subject to any disclaimer, the term of this patent is extended or adjusted under 35 U.S.C. 154(b) by 0 days.

(21) Appl. No.: 17/401,619

(22) Filed: Aug. 13, 2021

(51) Int. Cl.
*A61B 5/00* (2006.01)
*A61B 5/22* (2006.01)
*A61B 5/369* (2021.01)
*A61B 5/389* (2021.01)

(52) U.S. Cl.
CPC ............ *A61B 5/4557* (2013.01); *A61B 5/002* (2013.01); *A61B 5/228* (2013.01); *A61B 5/369* (2021.01); *A61B 5/389* (2021.01); *A61B 5/486* (2013.01); *A61B 5/4812* (2013.01); *A61B 5/4833* (2013.01); *A61B 5/6803* (2013.01); *A61B 5/742* (2013.01); *A61B 5/7405* (2013.01); *A61B 5/7455* (2013.01)

(58) Field of Classification Search
CPC ....... A61B 5/4557; A61B 5/369; A61B 5/389; A61B 5/002; A61B 5/228; A61B 5/4812; A61B 5/4833; A61B 5/486; A61B 5/6803; A61B 5/7405; A61B 5/742; A61B 5/7455
See application file for complete search history.

(56) References Cited

U.S. PATENT DOCUMENTS

| | | | |
|---|---|---|---|
| 8,160,689 B2 * | 4/2012 | Jadidi | A61B 5/6814 600/546 |
| 10,285,636 B2 * | 5/2019 | Singer | A61B 5/389 |
| 2006/0184059 A1 * | 8/2006 | Jadidi | A61B 5/4557 600/546 |
| 2017/0135626 A1 * | 5/2017 | Singer | G06T 7/0016 |

* cited by examiner

*Primary Examiner* — Jonathan T Kuo
(74) *Attorney, Agent, or Firm* — Nasser Ashgriz; UIPatent Inc.

(57) ABSTRACT

The present invention is method and a device to detect and treat Bruxism through a combination of muscle and brain sensors detecting sensors and providing a set of biofeedbacks to stop grinding while preventing habituation to biofeedbacks. The frequency and phase of the rhythmic grinding pattern of a Bruxer is identified and a biofeedback with the same frequency but different phase is applied on the user to stop grinding without waking the user from a sleep.

11 Claims, 4 Drawing Sheets

DEVICE AND METHOD FOR DETECTION AND TREATMENT OF BRUXISM

FIELD OF THE INVENTION

The present invention relates to devices and methods for monitoring, preventing and treating tooth grinding or Bruxism.

BACKGROUND OF THE INVENTION

Bruxism is a repetitive jaw-muscle activity characterized by clenching or grinding of the teeth and/or by bracing or thrusting of the mandible that could happen during awake and sleep periods. Bruxism is a common behavior that more than 10% of adults and 15% of children suffer from. Bruxism is often undetected and the first indication often comes from the dentist who recognizes the damage to the teeth. Several symptoms are commonly associated with bruxism, including hypersensitive teeth, aching jaw muscles, headaches and damage to dental restorations crowns and to teeth. Tooth grinding may also cause temporomandibular joint disorder (TMD). The exact cause of bruxism is still not known, but it is mainly related to anxiety and stress.

Currently, there is no specific cure for Bruxism, however, there are several different treatment systems. One set of treatments include splints and mouth guards. Others include: Occlusal splint, physical therapy, stretching exercises, ultrasonography, behavioral therapy and low laser therapy. There are also invasive treatments including: Acupuncture, dry needling, injection of a local anesthetic or saline and BTX (Botox) injections. Traditional passive treatment methods such as occlusal splints only prevent enamel damage from teeth grinding but fail to treat bruxism from the root.

Another group of treatments is through using a biofeedback to stop grinding. Biofeedback systems use a sensor, such as an electromyography (EMG) or an Electroencephalography (EEG) to detect jaw muscle movement or a microphone to detect the grinding sound, and then trigger a biofeedback, such as a vibrator to alert the grinder to stop grinding. These devices lose their effectiveness overtime due to habituation, and the user does not response to the biofeedback. To keep them effective, the amplitude of the biofeedback has to be increased so much so that it will interfere with the user's sleep, so that they stop using them.

SUMMARY OF THE INVENTION

The present invention discloses a method and a device in the form of a smart sleep mask or a headband, that detects the Bruxism through various detecting sensors and provides a biofeedback treatment without disturbing user' sleep to treat the Bruxism and prevent habituation to a biofeedback.

The method comprises of measuring a temporalis muscle activity using a set of muscle sensors; identifying a grinding threshold by having a user grind teeth and measuring a bite force by the set of muscle sensors; activating a set of brain signal sensors when the grinding threshold measured by the set of muscles sensors is reached when user is sleep; measuring a brain activity using the set of brain signal sensors; analyzing the brain activity by a microprocessor configured to identify a brain signal rhythmic pattern characterized by a frequency, a phase and an amplitude; generating and applying a biofeedback, having a biofeedback type and having the same pattern but being out of phase with respect to the brain signal rhythmic pattern; comparing a new brain activity received after applying the biofeedback with the brain activity before applying the biofeedback, if the new brain activity a rhythmic pattern, randomly change the phase, the frequency, and the amplitude of the biofeedback rhythmic pattern until the brain activity is not rhythmic, and changing the biofeedback type in a cycle of sleep if the temporalis muscle activity or the brain activity show a habituation pattern.

The presently disclosed sleep mask/headband comprises of the following main elements: A set of EMG (Electromyography) or a set of EEG (Electroencephalography) sensors to detect muscle activities; and a set of EEG sensors to detect the brain activity; a set of biofeedback devices to alert the Bruxer, and a processor to analyze all signals and operate the biofeedback systems to stop Bruxism, while preventing habituation to the biofeedback signals. The biofeedback methods are used as actuation to relax jaw muscles when unconscious grinding occurs, which will eventually train the brain to stop grinding.

A combination of EEG and EMG sensors are installed to differentiate between Bruxism activity of muscles and other masticatory muscle activity, such as yawning and swallowing. It also has a novel method of analyzing both EMG and EEG signals to detect the occurrence of the tooth grinding, determining the best biofeedback to stop the Bruxism, and preventing habituation to the biofeedback.

The device has a Bluetooth capable microprocessor that links to the user's phone through Android and IOS applications. Sleep related signals are recorded on the phone and can be seen later. Users can program their treatment method by selecting their preferred feedbacks, adjusting their therapy and visually tracking their progress. The biofeedback signal methods are pre-programmed to be changed in a cycle of sleep to prevent the common habituation problem.

The users can adjust their therapy and track their progress, by viewing reports on how many times they grinded or clenched their teeth the previous night. Additionally, the user will be able to see how well their therapy is progressing over time by comparing nightly events of bruxism over the course of several days or weeks.

The present invention includes several novelties to identify and stop grinding. One that it uses a combination of muscle and brain activity to differentiate between bruxism activity of muscles and other masticatory muscle activity, such as yawning and swallowing. It also has a novel method of analyzing both the muscle signals and brain signals to detect the occurrence of the tooth grinding, determining the best biofeedback to stop the Bruxism, and preventing habituation to the biofeedback.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF PREFERRED EMBODIMENTS

Figure 1:
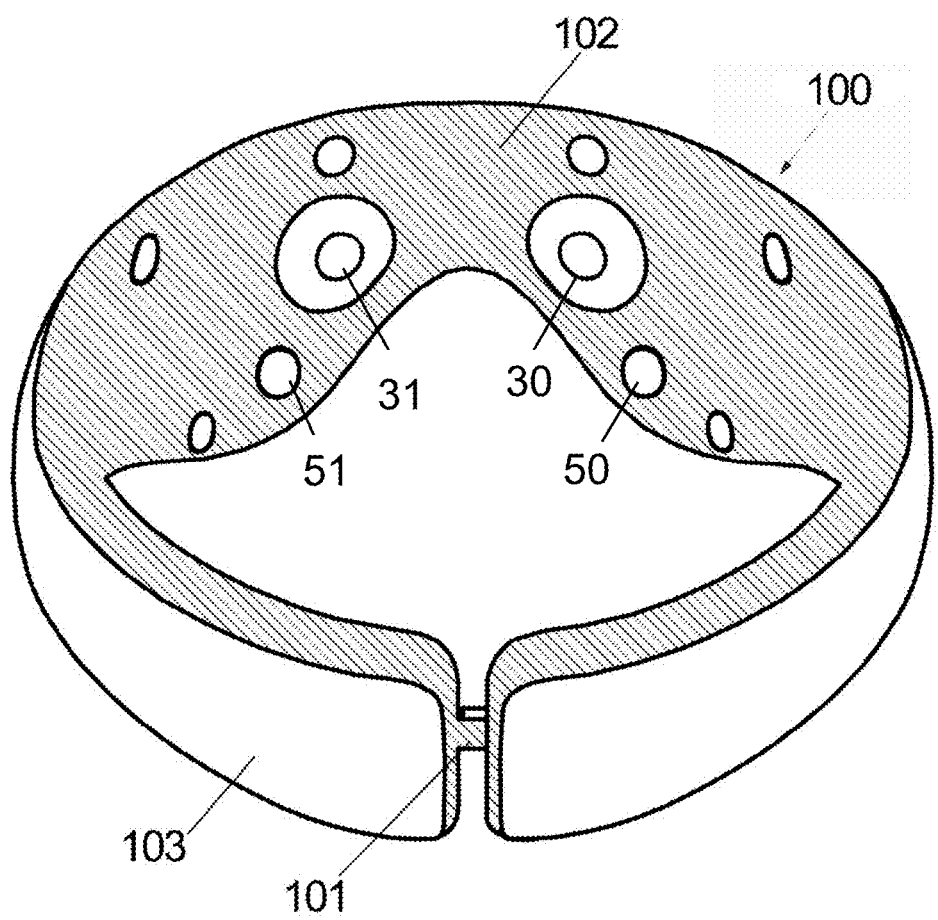
FIG. 1 shows a perspective view of a preferred embodiment of the smart sleep mask of the present invention.

According to FIG. 1 the present invention is a smart sleep mask (or headband) 100 wearable by a user to measure grinding activities using a detection system with a set of sensors and generate feedback signals using a biofeedback system. The headband can also be used both for sleep and awake bruxism. In one embodiment, the smart sleep mask 100 completely surrounds the head and is adjustable to fit on each user by adjustable straps 101 or any suitable means on the rear portion to allow for a fit on each user's head. The mask 100 may be made from stretchable fabrics to provide comfortable wear for the user, and preferably made from a soft fabric material such as cotton, polyester, nylon or silk. Using the masks also helps the user relax and reduce stress. Stress is known to be one of the causes of Bruxism.

The mask 100 is constructed in two layers, an outer layer 103 and an inner layer 102. Each layer has a foam padding to provide comfortable cushioning. A detection system and a biofeedback system and all electrical components are installed in between the layers in the specific position. The components are selected from light-weight devices to achieve a light weight and ultra-small size so that the mask does not disturb user's sleep.

Figure 2:
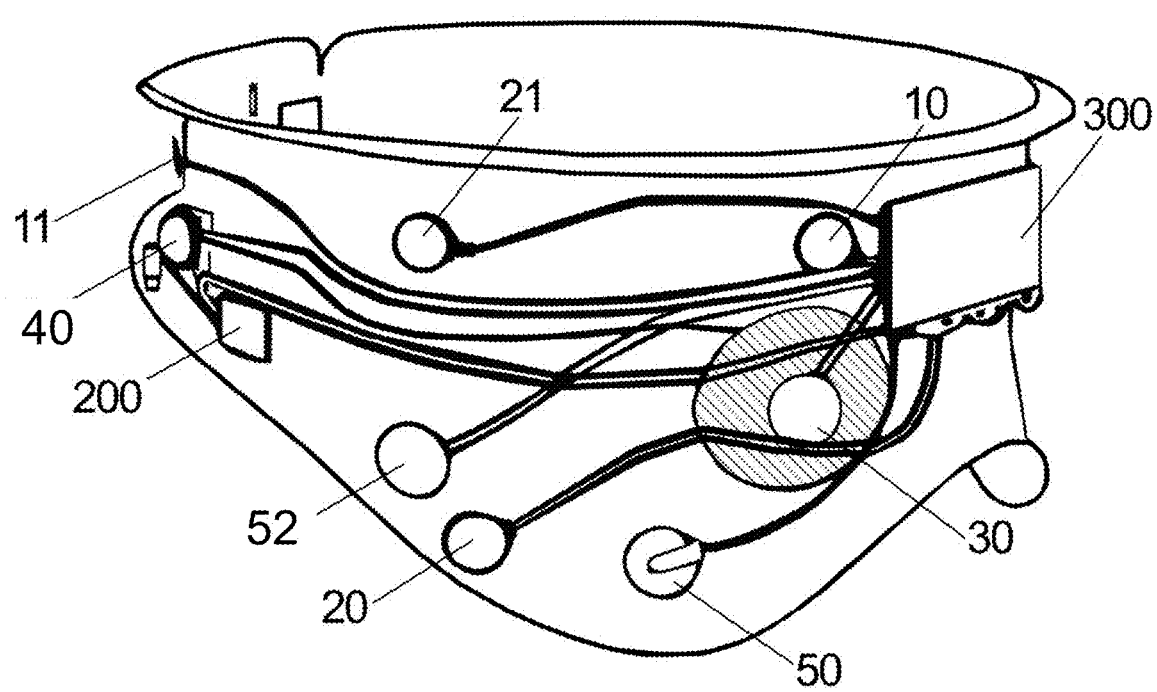
FIG. 2 is a schematic diagram showing the components of the present device.
Figure 3:
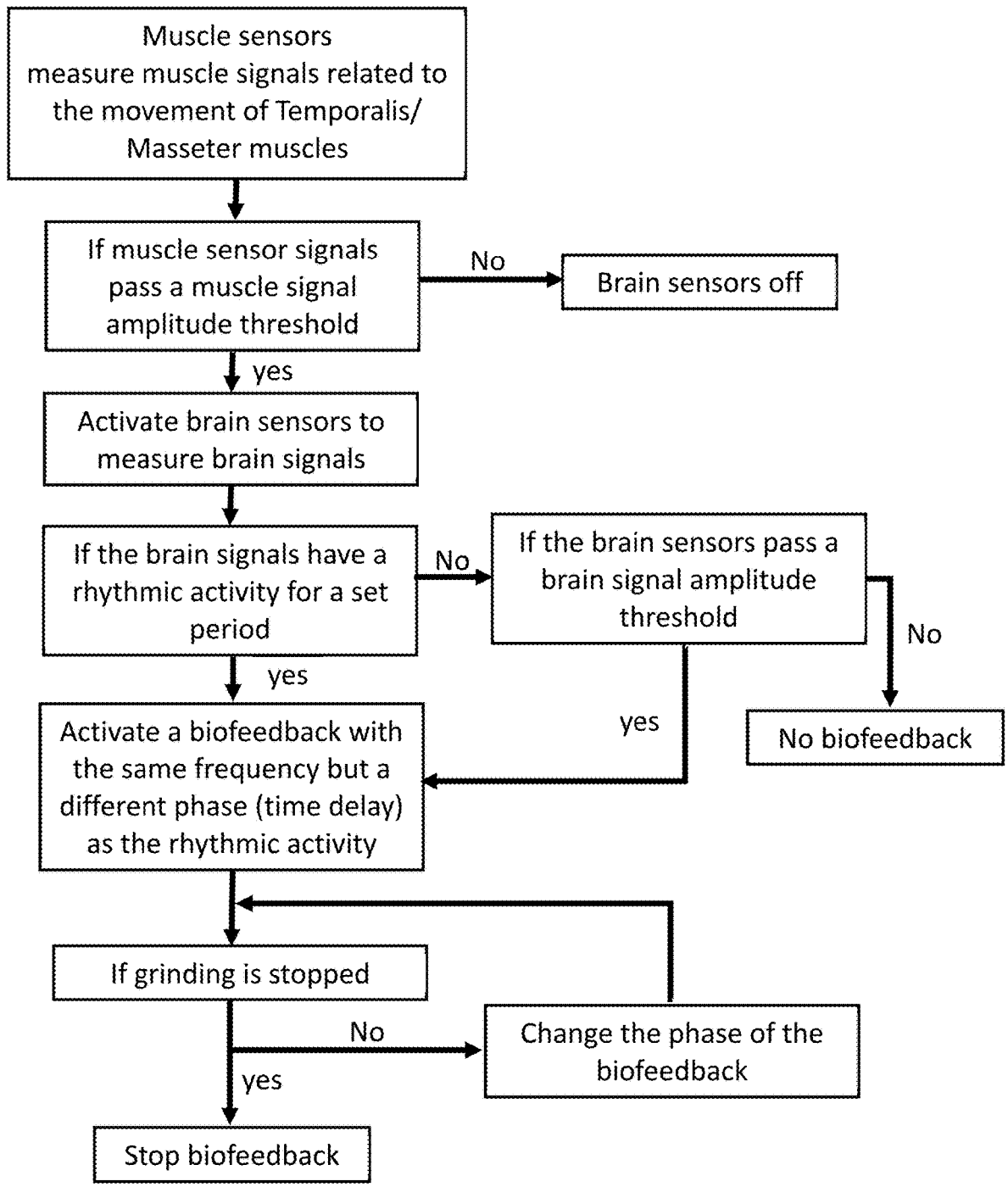
FIG. 3 is a perspective view showing the location of the components of the present invention.

According to FIGS. 2 and 3, the device 100 has a power supply system 200, and a processor 300, to control the operation of the device. R has a detection system that comprises of a set of muscle sensors and a set of brain sensors. The muscle sensors measure the muscle activity, and they are any one of an EMG (Electromyography) or EEG (Electroencephalography) sensors or any other types. The brain sensors comprise of EEG sensors or any other types to detect the brain activity. EEG sensors may be a fabric or a stainless-steel passive or dry biosensor types.

The biofeedback system comprises of a variety of biofeedback devices to alert the Bruxer. The signal processing unit 300 analyzes all signals and operates the biofeedback system to stop bruxism, while preventing habituation to the biofeedback signals. The biofeedbacks are used as actuation to relax jaw muscles when unconscious grinding occurs, which will eventually train the brain to stop grinding.

FIG. 2 shows the preferred locations of the units in the mask. In the preferred embodiment, two muscle sensors 20, 21 are attached to the mask on temporalis muscles area on each side of the mask 100. The muscle sensors 20, 21 can be selected from various sensors, including EMG, EEG, piezo disc type muscle sensors, piezo film muscle sensor, or a pressure resistive material that is woven into the mask/headband, to detect pressure in temporalis muscle. When the temporalis muscle moves, the sensors sense the movement. The movement information is transmitted through a series of wires to the microprocessor 300 and the microprocessor analyzes the movement information to determine if Bruxism is occurring.

It is to be understood that the number of sensors can be increased in other embodiments of the present invention. Placement of the muscle sensors 20, 21, over the temporalis muscle are the best placement, however sensors can be placed on masseter area of the mask/headband. One location is above and slightly behind the eye on the front portion of the mask to detect temporalis muscles on either side. Above the jaw muscles and behind the mouth on the masseter muscles is another optimum location. Placement of the muscle sensor over the temporalis muscle, just above the ear is the most desired placement in detecting bruxism. The temporalis muscle just above the ear only contracts when the back teeth are clenched or grinding. Therefore, it negates any interference the sensor would receive due to normal facial movements like talking or facial expression such as raising one's eyebrows.

A set of brain sensors 10 and 11 are used to measure the brain activity. The brain sensors are also strategically located on the forehead (with a grounded electrode on the ear) to optimize the brain signal measurement.

The biofeedback system of the present device is designed to prevent habituation. The biofeedback system comprises of a visual feedback through lights 30 located over the eyes, a sound biofeedback through a set of speakers 40 located over the ears, and a vibration biofeedback through a set of vibrators 50, 51 located over the jaw muscles. In some embodiments, more than one vibrator can be placed at different locations, such as 52 in FIG. 2. The biofeedback system is pre-programmed to be changed in a cycle of sleep to prevent the common habituation problem. The following changes are programmed: (i) Visual feedback in the form of LED lights 30, set in front of each eye, that changes in flashing pattern, light brightness, and light color. In one embodiment, the light comprises of a multiple small LED lights that have different colors. The headband does not have visual feedback. (ii) The auditory feedback in the form of a sound through a set of speakers 40 that changes in the volume, and the type of sound, such as beeps or music, and the location of the sound. (iii) The vibration feedback through a set of vibrators 50, 51 that change in frequency and amplitude. For example, the vibration duration is randomly set from 0.3 seconds to 3 seconds in a 3-second periods. This is the default setting and can be changed by the user. The system can also be programmed to combine several forms of feedbacks in order to prevent habituation to a feedback type.

FIG. 3 shows an operation process of the device and method of using the device for monitoring, preventing and treating bruxism. In the treatment plan, the system has to be calibrated for individuals. First both the muscle sensors and the brain sensors are calibrated using user's voluntary grinding and normal brain activity. The muscle sensors sense the temporalis muscle activities, which correlate to the tooth grinding and the bite force. The user is asked (through the application on a mobile phone) to bite and clench for a set period of at least for 5 seconds, while the muscle sensors (EMG) and brain sensors (EEG) record the signal. The muscle sensors 600 sense the movement of temporalis or masseter muscles 601 and the EEG sensors sense the electrical potential of the brain. The average amplitude of the signal measured by the muscle sensors when the user voluntarily clenches and grinds is set as the user's muscle biteforce. The processor 300, analyzes all signals received and assigned a first threshold as a fraction of the user's muscle biteforce. A preferred fraction is set in a range of ⅕ to ⅓, and preferably ⅓ of the measure biteforce. When the system is used, during sleep or awake, once the biteforce passes this first threshold, the brain sensors are turned on. Before this threshold, the brain sensors are kept off to save battery power. And, once again, while the brain sensors are on and the muscle sensors measure biteforces less than the threshold, the brain sensors are turned off.

The brain sensors are also used while the user is awake to calibrate the sensor values. The normal frequencies of the brain signals include delta (0-4 Hz), theta (4-7 Hz), alpha (7-14 Hz), beta (15-30 Hz), and gamma (30-100 Hz) waves. Once the set of brain sensors are on, they will continuously measure the brain activity during grinding. When the user is grinding, a rhythmic masticatory muscle activity (RMMA) occurs. Also, the muscle sensor record signal amplitude above the threshold levels. In addition, the RMMA generally occurs repeatedly, many times during a short period of time. A value is preset for the number of occurrences of rhythmic patterns to identify RMMA. This values is set as 4 times in a period of 10 seconds, however, it can be changed by the user or by a machine learning algorithm.

The average amplitude of the all the signals measured by the brain sensors during the user voluntary clench and grind, in the system calibration period, is determined and set as the brain biteforce. A second threshold is defined as a multiple of the brain biteforce. The preferred multiple is in the range of 1.5 to 2 times of the brain bite force, and preferably 1.7 times of the brain bite force.

When the brain sensors are on, the brain signals are received and analyzed by the microprocessor 300. The microprocessor is configured to identify a rhythmic pattern in the brain signal. A non-linear time-frequency transformations allow for the extraction of different features of the signal. A classifier converts the data into the frequency domain using a Fast Fourier Transform (FFT) algorithm. The normal signals measured during the calibration are filtered out of the measured signal. A non-linear classifications algorithm uses the remaining features to determine any rhythmic pattern in the signals. The microprocessor is configured to determine the frequency, the phase and the amplitude of the identified rhythmic pattern. The occurrence of the bruxism event is based on determining whether the brain activity has a sustained rhythmic activity. The rhythmic pattern usually has a frequency between 0.1 and 1.5 hertz (Hz). If a rhythmic pattern is identified, its frequency and phase are set as the grinding frequency and grinding phase.

Once the grinding rhythmic pattern is identified, a set of biofeedbacks 603 are generated by the processor that have the same rhythmic pattern as the grinding rhythmic pattern, but at a different phase. Therefore, as the Bruxer grinds his/her teeth in a rhythmic pattern with a grinding frequency f and a grinding phase $\phi$, a biofeedback with a frequency f and a phase $\phi+\phi_b$ is applied. The phase is basically a time delay in the application of the biofeedback. The phase is larger than zero and less $\pi$, and it changes randomly between these values until the grinding is stopped. One advantage of this biofeedback is that it stops grinding at relatively low biofeedback amplitudes, which do not disturbed user's sleep.

The brain activity after the application of a biofeedback is compared with those before the application of the biofeedback to determine if the rhythmic pattern is stopped. If not, the biofeedback phase and then amplitude are changed until the grinding stops.

In case the processor cannot identify a rhythmic pattern in the brain signals, but the muscle sensors show continuous muscle activity at levels above the first threshold, the biofeedback system is triggered using the second threshold. In this case the multiple of the average measured amplitude of the brain signal during system calibration is used to trigger the biofeedback system.

In one embodiment, a machine Learning Algorithm is used for self-learning and updating the user's personal data as new data becomes available. The new data comprise of different characteristics of the brain signal during grinding period, including the amplitudes of the signal during grinding and its rhythmic pattern. A "classifier" (refers to an algorithm that categorizes data based upon a set of features extracted from the data) extracts certain features from the data, and is trained based on the actual data to distinguish between the categories.

The microprocessor is also configured to check the number of rhythmic grinding episodes in a sleep cycle. If the number of the rhythmic grinding episodes increases, the biofeedback is changed and its effect on the grinding is checked. Increase in the number of episodes is an indication of user habituation to the feedback.

The signal processing system 300 passes the signals through a rectifier and an integrator to identify the main episodes, and to extract unique features of the signal. The processor interprets the signals by statistics and signal processing and send feedbacks to the user. The feedbacks in the form of auditory, vibration and visual can be adjusted by the user for their therapy. The user can adjust the intensity of the vibration or light flashes, as well as the volume of the sound. The users can track their progress, by viewing reports on how many times they grinded or clenched their teeth the previous night. Additionally, the user will be able to see how well their therapy is progressing over time by comparing nightly events of bruxism over the course of several days or weeks.

The vibration feedback signals is programmed to have a varying frequency and pattern or amplitude every time it is turned on to prevent the common habituation problem. The vibration duration is randomly set from 0.3 seconds to 2.7 seconds in a 3-second period to vary the frequency and is determined based on experimental testing. This range could be changed in the code for different individuals for best results. The duration of the vibration is pre-programmed to a different method each time the device is turned on. The vibrators have a micro vibration motor that features quiet and consistent vibration feedback implemented in the system.

Visual feedback is pre-programed in the form of LED lights-change to change in colors, change in flashing and frequency, change in intensity, etc. This can be pre-set to produce various visual feedback to alert the user and prevent of habituation. Several forms of feedback are combined in a cycle of sleep in order to prevent the user's brain get habituated to the feedback.

Figure 4:
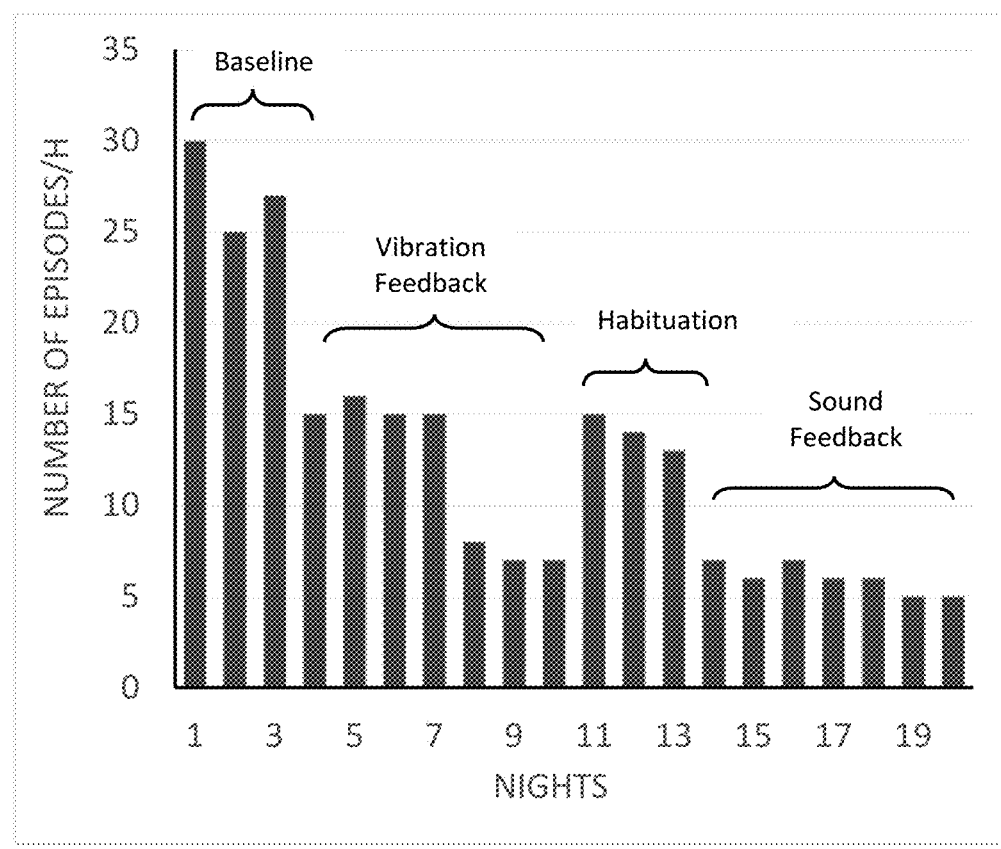
FIG. 4 is a chart of a signal testing result showing the number of grinding episodes per night.

FIG. 4 shows how a habituation is recognized. The figure shows the change in the number of tooth grinding episodes per hour over a 20 nights period. The user did not have the mask on for the first three nights, to identify sleep time tooth grinding. The number of episodes are then recorded (for example, 27 episodes per hour in FIG. 4). After a vibrational biofeedback, the number of episodes dropped to about 15/hr for the next 4 nights and then to 6/hr for the 3 nights after that (note each user's response to biofeedback is different). The number of episodes increased back to 15/hr from the 11th night. The microprocessor identified the increase in the number of episodes and changed the biofeedback to sound. The number of episodes reduced back to 6/hr, preventing habituation.

The system and method of the present invention uses machine learning algorithm for developing the most effective biofeedback for each user. If the number of grinding episodes starts to increase, the system will change the feedback mechanism to reduce grinding. The machine learning algorithm will also learn overtime about what brain signal is triggered shortly after it occurs. Therefore, the EEG sensor detects the electrical activity in the brain before the jaw muscles tightens, and the feedback devices can activate just on time when the muscle tightens. This will train the brain to relax and calm the jaw muscles. Therefore, the biofeedback can be sent before the grinding starts. Implementing Machine Learning and AI can improve to better understand sensor signals.

The biofeedback system associates with the subconscious mind, to instinctively stop clenching. The user can exercise a few minutes while awake using the application of the device each day. This creates and strengthens the part of the subconscious that will work with the smart mask to stop clenching. The feedback signals act like brake lights for the clenching and grinding, because the subconscious has been trained. After a little practice the brain learns to respond to the feedbacks.

The system further comprises of a user's manual and an application installed on the user's phone that takes the user through a series of screens to calibrate the feedback devices and to teach the user the meaning of each chart. The device may include a touch button paired with the mobile application to adjust and control the feedback devices. The device has to be set properly on the head in order to measure properly. Once the mask is put on, all device connections are checked so that the conductance between the device and skin is less than 10 k$\Omega$. If the conductance is larger than 10 k$\Omega$ a red light or a beep sound alerts the user to adjust the location of the mask until a double beep sound is heard alerting proper connection. In one embodiment, the LED lights 30 turn red and green to alert the user if the devices is set improperly or properly, respectively. If a headband is used, the muscle and brain signals can be observed in real time to calibrate the devices.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A device to detect and treat bruxism, comprising;
   a) a set of muscle sensors to measure a series of muscle signals;
   b) a set of brain sensors to measure a series of brain signals;
   c) a biofeedback system to provide a set of biofeedback signals to a bruxer to stop a teeth grinding, the biofeedback system comprising:
      i) a visual feedback system in the form of LED lights;
      ii) an auditory feedback system in the form of sound through a set of speakers, and
      iii) a vibration feedback system through a set of vibrators,
   d) a microprocessor configured to
      i) identify a rhythmic grinding pattern in the series of brain signals and determine a frequency, a phase and an average amplitude of the rhythmic grinding pattern, and activate the biofeedback system with a biofeedback frequency that is the same as the frequency of the rhythmic grinding pattern but have a biofeedback phase shift (time delay) with respect to the phase of the rhythmic grinding pattern,
      ii) randomly change the set of biofeedback signals until the series of brain signals is not rhythmic, and
      iii) change the biofeedback system between the visual, the auditory, and the vibration feedback systems in a cycle of sleep if a temporalis muscle activity or the series of brain signals show a habituation pattern.

2. The device of claim 1, wherein the set of muscle sensors comprise of any one of electromyogram (EMG) sensors, a piezo disc type muscle sensors, piezo film muscle sensor, or a pressure resistive material that is woven into the mask/headband, and the set of brain sensors comprise of electroencephalography EEG sensors.

3. The device of claim 2, wherein the EEG sensor is a fabric, or a stainless steel passive, dry biosensor.

4. The device of claim 1, wherein the device is a wearable sleep mask or a headband.

5. The device of claim 1, wherein the LED lights are configured to change in a flashing pattern, a light brightness, and a light color, the auditory feedback is configured to change in a sound volume, a type of sound, and a left or a right ear sounds, and the vibration feedback is configured to change in a vibration frequency and a vibration amplitude.

6. The device of claim 1, further comprising one or more transmitter and/or receiver, one or more data storage unit capable of recording bruxism event data and non-bruxism event data, and a power control unit to supply power to the device.

7. The device of claim 6, wherein the power control unit comprising a replaceable, a rechargeable or a disposable battery, or a non-battery power supply converting vibrations or radio waves into power.

8. The device of claim 6, wherein the receiver is a smartphone, a tablet or a desktop.

9. The device of claim 6, further having a BLUETOOTH capable microprocessor that links to the receiver through ANDROID and IOS applications.

10. The device of claim 6, wherein the device is configured to:
    a) collect data and transmit to the receiver, wherein long term data is collected on an ongoing basis for the user to monitor the process of user's grinding;
    b) provide a nightly, weekly and monthly history of user's grinding;
    c) provide an assessment of users improvement and suggest a treatment program based on user's history, whereby the user monitors and tracks the treatment procedure and can customize user's treatment program.

11. The device of claim 6, having a Wi-Fi communication to transfer data between the device and the receiver.

* * * * *